(12) United States Patent
Weiner

(10) Patent No.: US 6,488,561 B2
(45) Date of Patent: *Dec. 3, 2002

(54) HEATED STUFFED ANIMAL

(76) Inventor: George A. Weiner, 7933 Harwood Pl., Springfield, VA (US) 22152

( * ) Notice: Subject to any disclaimer, the term of this patent is extended or adjusted under 35 U.S.C. 154(b) by 0 days.

This patent is subject to a terminal disclaimer.

(21) Appl. No.: 09/986,661

(22) Filed: Nov. 9, 2001

(65) Prior Publication Data

US 2002/0028627 A1 Mar. 7, 2002

Related U.S. Application Data

(63) Continuation-in-part of application No. 09/549,587, filed on Apr. 14, 2000, now Pat. No. 6,325,695.

(51) Int. Cl.$^7$ ................................................. A63H 3/02
(52) U.S. Cl. ..................... 446/369; 219/201; 446/295
(58) Field of Search ................... 446/369, 295, 446/484, 74, 14, 270, 371, 296, 72–73; 219/549, 528, 529, 200, 201

(56) References Cited

U.S. PATENT DOCUMENTS

| | | | |
|---|---|---|---|
| 1,558,278 A | 10/1925 | Phillips | |
| 1,896,663 A | * 2/1933 | Collins | |
| 2,647,195 A | 7/1953 | Broyles | 219/19 |
| 2,859,731 A | 11/1958 | Sutton | 119/1 |
| 3,888,233 A | 6/1975 | Ware | 128/1 |
| 4,204,110 A | * 5/1980 | Smit et al. | 219/313 |
| 4,300,307 A | * 11/1981 | Biasuzzi et al. | |
| 4,694,829 A | * 9/1987 | Frye | 128/399 |
| 4,714,445 A | * 12/1987 | Templeton | 446/74 |
| 4,718,876 A | 1/1988 | Lee | 446/295 |
| 4,954,676 A | 9/1990 | Rankin | 219/200 |
| 4,968,281 A | 11/1990 | Smith et al. | 446/369 |
| 4,979,923 A | * 12/1990 | Tanaka | 446/72 |
| 5,002,511 A | 3/1991 | Maki | 446/14 |
| 5,066,259 A | * 11/1991 | Acker | 446/385 |
| 5,471,192 A | * 11/1995 | Dash | 340/384.3 |
| 6,325,695 B1 | * 12/2001 | Weiner | 446/369 |

* cited by examiner

Primary Examiner—Derris H. Banks
Assistant Examiner—Jamila Williams
(74) Attorney, Agent, or Firm—Wenderoth, Lind & Ponack, L.L.P.

(57) ABSTRACT

A heated stuffed animal is provided for therapeutic use which includes a soft body having an inner cavity and an outer covering, said outer covering having an appearance of a live animal, an electric heating pad disposed within said inner cavity for generating heat, said electric heating pad including an electric power cord projecting outside of said outer covering for connection to an AC electric outlet power supply, means for selecting a temperature of heat generated by said electric heating pad, and a ballast material disposed within said inner cavity.

18 Claims, 2 Drawing Sheets

HEATED STUFFED ANIMAL

This application is a continuation-in-part of Ser. No. 09/549,587 filed Apr. 14, 2000. Now U.S. Pat. No. 6,325,695.

BACKGROUND OF THE INVENTION

1. Field of the Invention

This invention relates to a heated stuffed animal, and particularly to a stuffed animal containing an electric heating pad for therapeutic use.

2. Description of Related Art

A variety of heated stuffed animals are known in the art. For example, U.S. Pat. No. 1,558,278 discloses a combined toy and heating device in the shape of a stuffed animal containing a hot water bottle or electric heating means. U.S. Pat. No. 1,896,663 discloses an electrically heated toy in the shape of a doll or animal which is warmed by an electric resistance wire or heating pad. U.S. Pat. No. 2,647,195 discloses a sleeper toy in the shape of an animal such as a teddy bear containing an electric heating pad. U.S. Pat. No. 2,859,731 discloses a puppy comforter in the shape of a mother dog containing a resistance wire heating element. U.S. Pat. No. 4,204,110 discloses a decorative personal electric heating appliance in the shape of a stuffed-animal containing a bladder filled with a heatable fluid. U.S. Pat. No. 4,694,829 discloses a therapeutic stuffed toy in the shape of an animal figure such as a teddy bear containing a hermetically sealed container filled with a non-toxic heatable or chillable fluid. U.S. Pat. No. 4,714,445 discloses a warmed animal toy in the shape of an animal such as a teddy bear containing a bladder filled with a heatable fluid. U.S. Pat. No. 4,954,676 discloses a battery powered electrically heated stuffed toy containing a mass of fibrous heat transfer material such as a mass of copper wires. U.S. Pat. No. 5,002,511 discloses a stuffed animal toy containing a heating element responsive to infrared radiation such as a ceramic material.

None of the prior art heated stuffed animals, however, disclose or suggest the combination of features of the heated stuffed animal of the present invention, as is described hereinbelow.

SUMMARY OF THE INVENTION

The object of this invention is to provide an electric heating pad which has all of the therapeutic benefits and features of a modern electric heating pad, while providing the additional benefits of being comforting to the user. The user is envisioned to be an adult or child in need of therapeutic heat application to a sore or tender part of their anatomy.

The heated stuffed animal of the present invention has the following combination of features which is not suggested by the prior art. The heated stuffed animal comprises a soft body having an inner cavity and an outer covering. The outer covering has the appearance of a live animal, preferably a household pet such as a dog or cat. Within the inner cavity of the stuffed animal is disposed an electric heating pad for generating a therapeutic amount of heat. The electric heating pad includes an electric power cord which projects through an opening in the outer covering for connection to an AC electric outlet power supply. The electric heating pad includes a means for selecting a temperature of heat generated by said electric heating pad. Preferably the means for selecting the temperature of the heat is a control device located on the electric power cord outside of the outer covering for ease of adjustment by the user. The electric heating pad also preferably contains a means for controlling the heat generated by the heating pad, such as a thermostat control which is preset to discontinue heating of the electric element upon the element reaching a specified temperature. Lastly, the heated stuffed animal contains a ballast material in the inner cavity which provides the stuffed animal with a sense of weight which is comforting to the user and evokes a sensation that the user is being warmed by a live animal. These and other features of the preferred embodiments of the invention are described hereinbelow in further detail.

DETAILED DESCRIPTION OF THE PREFERRED EMBODIMENT(S)

Figure 1:
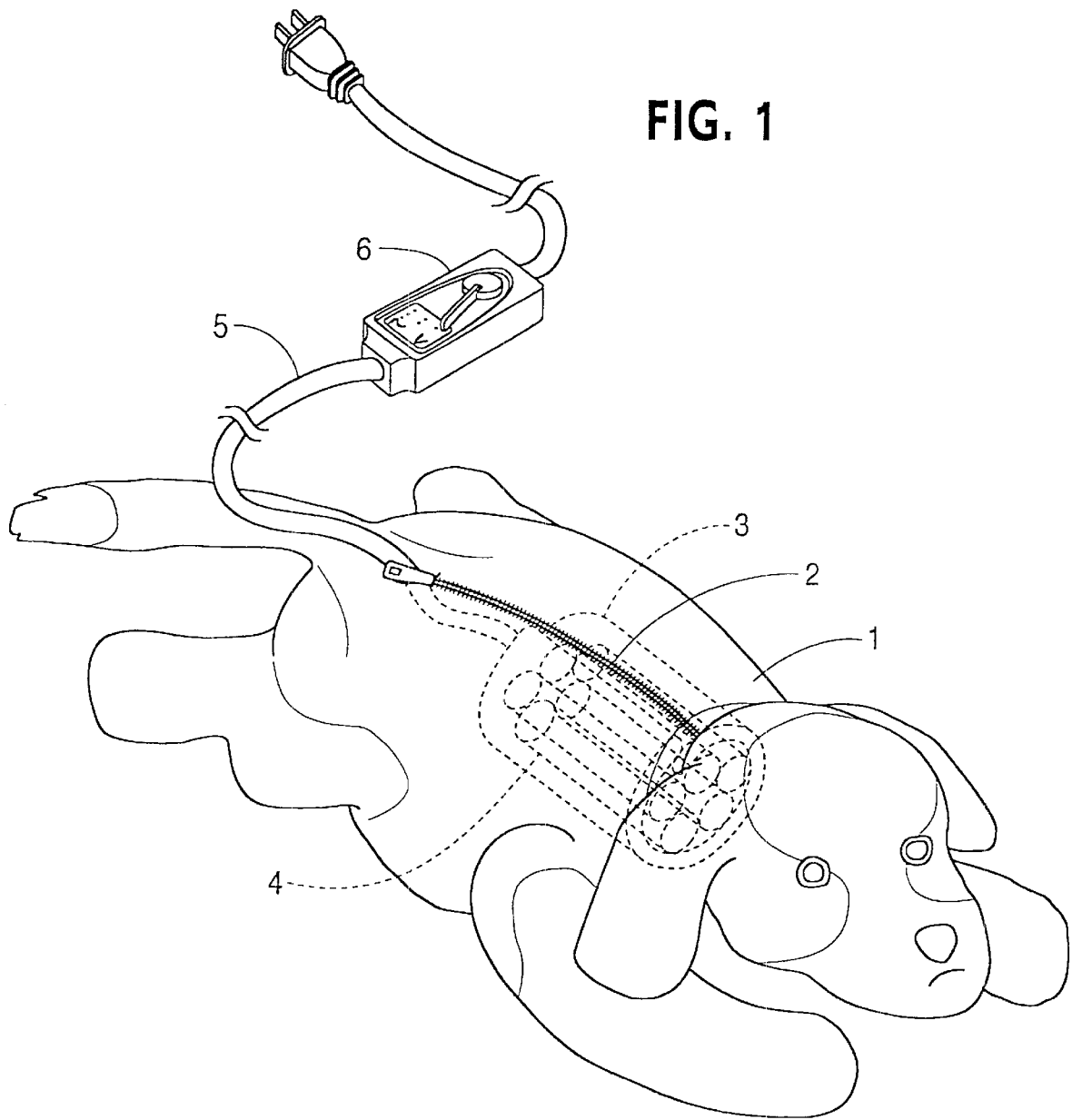
FIG. 1 is a perspective view of the heated stuffed animal which is a preferred embodiment of the invention identified as "LAPDOG" by the inventor, showing in broken lines the electric heating pad and ballast disposed within the inner cavity of the animal which features are hidden in use.
Figure 2:
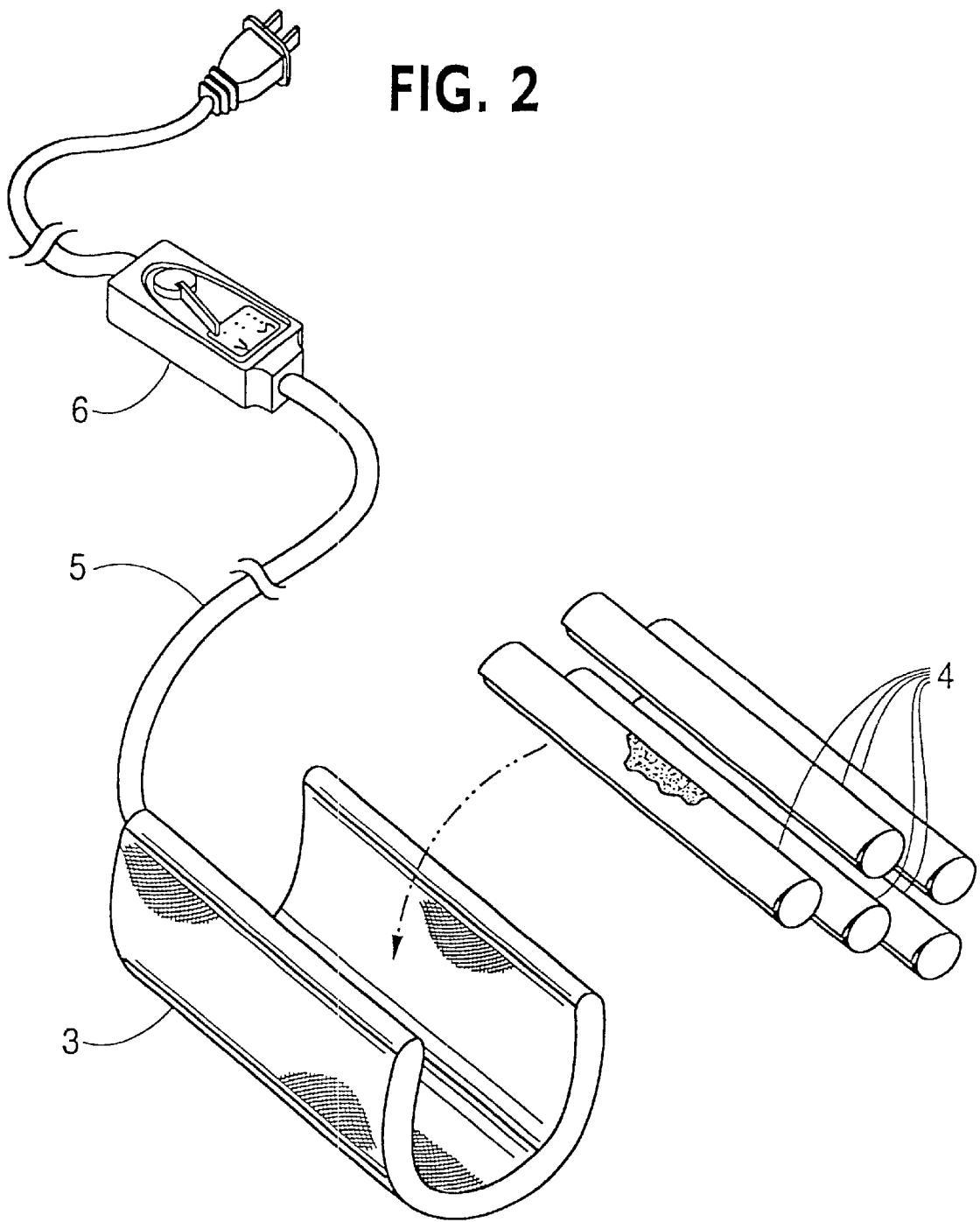
FIG. 2 is a perspective view of the electric heating pad, ballast, power cord and means for selecting a temperature of heat generated by the heating pad according to the preferred embodiment shown in FIG. 1.

A preferred embodiment of the invention is shown in FIG. 1. The heated stuffed animal has a soft body having an outer covering 1 which is constructed from conventional soft materials made from synthetic or natural fibers. Examples of synthetic materials are rayon, polyester, Dacron, etc. Natural fibers are cotton. Preferably the outer covering has a fur-like exterior and coloring which simulates the appearance of a live animal. The outer covering may alternatively be partially or solely made of a leather, plastic or other non-fur like material to simulate skin. Preferably the soft body is in the shape of a dog, but the body is also envisioned to be in the shape of essentially any animal such as a cat, lion, bear, monkey, giraffe, tiger, rhino, pig, etc.

The outer covering 1 has an opening 2 to allow access to an inner cavity of the stuffed animal. Preferably the opening 2 is large enough to permit replacement or repair of the electric heating pad 3 contained therein. For example the opening may be 8 to 12 inches long and be disposed longitudinally along the back of the stuffed animal, as shown in FIG. 1. Additionally the opening 2 serves to allow the user to add or remove ballast 4, allowing the user to choose the most comfortable weight of the stuffed animal for use as a heating pad. The electric heating pad 3 and ballast 4 are described in more detail hereinbelow. The opening is closed by any conventional means, such as a zipper, velcro, etc.

As mentioned above, an electric heating pad 3 is disposed within the inner cavity of the stuffed animal. The electric heating pad 3 may be any conventional construction. Preferably the electric heating pad 3 is waterproof and operates at 50 W and 120 V. The heating pad 3 is preferably located within the inner cavity of the stuffed animal, adjacent to the underside of the outer covering corresponding to the chest and belly of the stuffed animal. The heating pad 3 may be anchored to the inside of the outer covering to maintain its position and assure sufficient contact with the inside of the outer covering to enable a maximum heat transfer through the outer covering. Alternatively the heating pad 3 need not be anchored but be loose inside the inner cavity. The dimensions of the electric heating pad may be any which are suitable for fitting inside the stuffed animal. Preferably the electric heating pad 3 is about 10 to 12 inches by 10 to 12 inches. The heating pad 3 should be a sufficient size to generate a therapeutic amount of heat through the outer covering corresponding to at least the underside of the stuffed animal. Preferably the heating pad 3 is large enough to be folded or curled within the inner cavity so as to be in contact with the outer covering corresponding to the chest, belly, sides and back of the stuffed animal. In such embodiment the stuffed animal is warm to the touch over most of its body, helping to simulate a live animal and to provide better therapeutic heat to the user.

The electric heating pad 3 includes an electric power cord 5 for connection to an AC electric power supply. The power cord 5 may exit the stuffed animal through an opening in the outer covering located at any suitable point. Preferably the power cord 5 exits the outer covering through opening 2 described above. More preferably the power cord 5 exits the outer covering through an opening in the genital area or underside of the stuffed animal. It is envisioned that the user will use the heated stuffed animal while watching TV, reading, etc., in which case the user will usually be seated in a chair or sofa or resting in bed. The power cord 5 should have a sufficient length so that the user may plug the power cord into a household AC electric outlet while comfortably sitting in a chair, sofa or resting in bed.

The electric heating pad 3 includes a means 6 for selecting a temperature of heat generated by the electric heating pad 3. The temperature selecting means 6 may be any conventional switch or other control device for selecting the temperature of the heating pad 3. Typically the means 6 is a switch having 2, 3, 4 or more settings corresponding to, e.g., low, medium and/or high. Preferably the means 6 includes an on/off switch for turning the electric heating pad 3 on and off. In the preferred embodiment the switch has four positions corresponding to off, low, medium and high. Alternatively the means 6 may include a fully variable control device, e.g. a rheostat, for varying the temperature by smaller increments. The temperature selecting means 6 is preferably located on the power cord 5 outside of the outer covering of the stuffed animal. Such location makes it easy for the user to turn on and off the heating pad 3 and to select the desired temperature. The electric heating pad 3 may further include a thermostat control for regulating the temperature generated by the heating pad 3. This is a conventional feature of most electric heating pads and is separate and apart from the temperature selecting means 6.

A ballast material 4 is disposed within the inner cavity corresponding to the torso of the stuffed animal. The ballast material is not located in the paws or legs of the animal. The ballast material 4 may be any material which gives the stuffed animal a desired weight. In this regard, the general construction of the stuffed animal of this invention produces a lightweight stuffed animal. It is believed that the therapeutic benefits of the stuffed animal are improved if the weight of the stuffed animal is sufficiently heavy to ensure good contact between the heated surface of the stuffed animal and the portion of the user's body needing therapeutic heat application. Too light a weight of the stuffed animal does not give sufficient contact between the heated surface of the stuffed animal and the user's body. In addition, a secondary therapeutic benefit of the ballast is that the stuffed animal has a weight which simulates or gives the user an impression that he or she is being warmed by a live animal, particularly a comforting pet such as a dog or cat. In other words, the primary function of the ballast material 4 is to give the stuffed animal of this invention an increased weight. An optional second function of the ballast material is to act as a heat absorber to provide more continuous warmth during use.

The ballast material 4 may have a weight in the range of 1 to 40 lbs., preferably 5 to 20 lbs., more preferably 10 to 15 lbs. The ballast material may be in a liquid, semi-solid or solid form. Any liquid, semi-solid or solid material may be used so long as it is non-toxic. Examples of suitable materials are gels such as polymer gels, rubbers, foams such as open cell polyurethane foams, plastics, powders, granules such as sand, and larger particles such as beads. Mixtures of different ballast materials may also be used. Depending upon the choice of material, the ballast material 4 may be contained in a sealed pouch or a plurality of sealed pouches within the inner cavity of the stuffed animal. Alternatively, the ballast material need not be enclosed in a pouch when a pouch is not necessary, particularly where the material is a solid and non-particulate. Preferably the ballast material is soft, deformable and pliant itself and/or when enclosed in one or more pouches. The pouches may be any size or shape. Preferably the ballast is contained in a plurality of pouches in the shape of cylinders. Preferably the cylinders are 10 to 12 inches in length having a diameter of 1 to 2 inches. So as to not inhibit the heat transfer from the electric heating pad through the outer covering, the electric heating pad is preferably inserted into the inner cavity so as to be in contact with the outer covering of the stuffed animal, and the pouches are then inserted into the inner cavity and placed on top of the heating pad. The heating pad may be curled around the pouches, and the pouches may assist in keeping the electric heating pad in position within the inner cavity.

The heated stuffed animal may further contain within the inner cavity a fire resistant stuffing material. The fire resistant material is preferably fiberglass stuffing.

It will be readily understood that various modifications may be made to the heated stuffed animal of my invention without departing from the scope and spirit of this invention. Accordingly these modifications are considered to be within the scope of this invention.

I claim:

1. A heated stuffed animal comprising:
  a soft body having an inner cavity and an outer covering, said outer covering having an appearance of a live animal,
  an electric heating pad disposed within said inner cavity for generating heat, said electric heating pad including an electric power cord projecting outside of said outer covering for connection to an AC electric outlet power supply,
  means for selecting a temperature of heat generated by said electric heating pad, and
  a ballast material disposed within said inner cavity and partially enclosed by said electric heating pad said ballast material comprising a gel, a foam, a rubber, a powder, a plurality of beads, a liquid or a solid plastic, and said ballast material acting as a heat absorber to provide more continuous warmth during use and acting as mass to simulate a live animal.

2. The heated stuffed animal according to claim 1, wherein said outer covering has the appearance of a dog or cat.

3. The heated stuffed animal according to claim 1, wherein said inner cavity further contains a fire resistant stuffing material.

4. The heated stuffed animal according to claim 1, wherein said electric heating pad includes a thermostat control for regulating a temperature generated by said electric heating pad.

5. The heated stuffed animal according to claim 1, wherein said electric heating pad has opposed first and second sides, wherein said first side is in contact with said outer covering, and wherein said second side is in contact with said ballast material which is contained in sealed cylindrical pouches.

6. The heated stuffed animal according to claim 1, wherein said ballast material is a soft, pliant polymer gel.

7. The heated stuffed animal according to claim 1, wherein said outer covering has an appearance of a dog, and wherein said electric heating pad is disposed in contact with said outer covering corresponding to the dog's chest and belly.

8. The heated stuffed animal according to claim 1, wherein said outer covering includes synthetic hair simulating fur.

9. The heated stuffed animal according to claim 1, wherein said outer covering includes an opening for accessing said inner cavity.

10. The heated stuffed animal according to claim 9, wherein said opening includes a zipper for closing said inner cavity.

11. A heated stuffed animal comprising:
- a soft body having an inner cavity and an outer covering, said outer covering having an appearance of a live animal,
- an electric heating pad disposed within said inner cavity for generating heat, said electric heating pad including an electric power cord projecting outside of said outer covering for connection to an AC electric outlet power supply,
- means for selecting a temperature of heat generated by said electric heating pad, and
- a ballast material disposed within said inner cavity having a weight in a range of 5 to 20 pounds and comprising a gel, a foam, a rubber, a powder, a plurality of beads, a liquid or a solid plastic in at least one enclosed container.

12. The heated stuffed animal according to claim 11, wherein said outer covering has the appearance of a dog or cat.

13. The heated stuffed animal according to claim 11, wherein said inner cavity further contains a fire resistant stuffing material.

14. The heated stuffed animal according to claim 11, wherein said electric heating pad includes a thermostat control for regulating a temperature generated by said electric heating pad.

15. The heated stuffed animal according to claim 11, wherein said electric heating pad has opposed first and second sides, wherein said first side is in contact with said outer covering, and wherein said second side is in contact with said ballast material which is contained in sealed cylindrical pouches.

16. The heated stuffed animal according to claim 11, wherein said outer covering has an appearance of a dog, and wherein said electric heating pad is disposed in contact with said outer covering corresponding to the dog's chest and belly.

17. The heated stuffed animal according to claim 11, wherein said outer covering includes synthetic hair simulating fur, wherein said outer covering includes an opening for accessing said inner cavity, and wherein said opening includes a zipper for closing said inner cavity.

18. The heated stuffed animal according to claim 11, wherein said ballast material is a soft, pliant polymer gel.

* * * * *